United States Patent [19]
Pell

[11] Patent Number: 5,697,365
[45] Date of Patent: Dec. 16, 1997

[54] ENDOTRACHEAL TUBE CONSTRUCTION AND METHOD FOR INTUBATING A PATIENT

[76] Inventor: Donald M. Pell, P.O. Box 31647, St. Petersberg, Fla. 33732-1647

[21] Appl. No.: 588,369

[22] Filed: Jan. 18, 1996

[51] Int. Cl.⁶ .................................................. A61M 16/00
[52] U.S. Cl. ........................ 128/207.15; 128/207.14; 128/912; 604/96; 604/280
[58] Field of Search ................ 128/207.15, 207.14, 128/200.26, 911, 912; 604/96, 280, 264

[56] References Cited

U.S. PATENT DOCUMENTS

| | | | |
|---|---|---|---|
| 3,538,918 | 11/1970 | Eugelsher | 128/912 |
| 3,884,242 | 5/1975 | Bazell et al. | 128/207.14 |
| 4,056,104 | 11/1977 | Jaffe | 128/207.15 |
| 4,146,034 | 3/1979 | Gupta | 128/207.14 |
| 4,419,095 | 12/1983 | Nebergall et al. | 128/207.15 |
| 4,477,255 | 10/1984 | Pasztor et al. | 604/96 |
| 4,584,998 | 4/1986 | McGrail | 128/207.15 |
| 4,593,690 | 6/1986 | Sheridan et al. | 128/207.15 |
| 4,601,713 | 7/1986 | Fuqua | 604/280 |
| 4,637,388 | 1/1987 | Melendy | 128/207.14 |
| 4,683,879 | 8/1987 | Williams | 128/207.14 |
| 4,710,181 | 12/1987 | Fuqua | 604/280 |
| 4,769,006 | 9/1988 | Papantonakos | 604/96 |
| 4,850,348 | 7/1989 | Pell et al. | 128/207.15 |
| 4,917,667 | 4/1990 | Jackson | 604/96 |
| 4,977,894 | 12/1990 | Davies | 128/207.15 |
| 5,067,497 | 11/1991 | Greear et al. | 128/207.15 |
| 5,447,152 | 9/1995 | Kohsai et al. | 128/207.15 |
| 5,487,730 | 1/1996 | Marcadis et al. | 604/96 |
| 5,562,127 | 10/1996 | Panselow et al. | 604/264 |

FOREIGN PATENT DOCUMENTS

| | | | |
|---|---|---|---|
| 0596517 | 5/1994 | European Pat. Off. | 604/96 |
| 1399093 | 6/1975 | United Kingdom | 128/207.15 |

*Primary Examiner*—Vincent Millin
*Assistant Examiner*—V. Srivastava
*Attorney, Agent, or Firm*—David E. Dougherty

[57] ABSTRACT

An endotracheal tube construction includes an elongated kink resistant flexible tubular member having distal and proximal ends with a curved portion therebetween. The tubular member defines a major passageway or airway and a relatively small cuff inflating lumen which is parallel to the major passageway and disposed in the wall of the tubular member. The cuff inflating lumen is positioned within a portion of the wall which is subjected to tension as the tubular member is bent as opposed to being positioned in that portion of the wall which is under compression. In addition, the portion of the wall adjacent to the lumen is thicker than the wall in other portions of the tube so that the tube is less likely to kink or collapse during intubation of a patient. The endotracheal tube includes a beveled tip and is constructed and arranged so that the beveled tip can be rotated by twisting a portion of the tube which extends out of a patient's mouth or nose without kinking or collapsing the tube. In this way, the far end of the suction catheter can be biased in the direction of the selected bronchi.

14 Claims, 3 Drawing Sheets

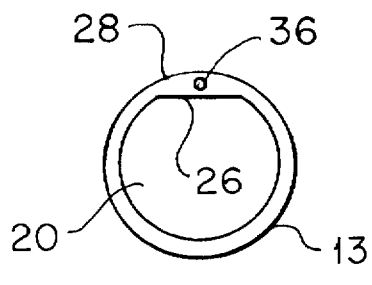
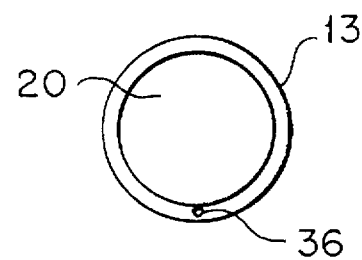
FIG. 6a                FIG. 6b
                       PRIOR ART
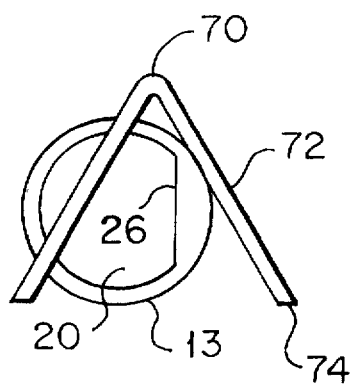
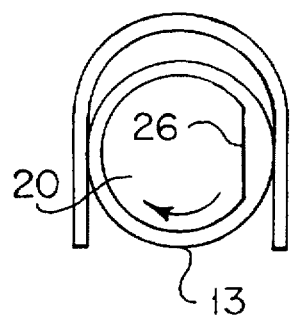
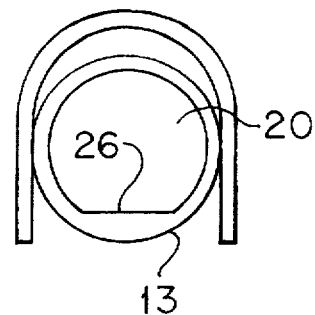
FIG. 7a     FIG. 7b     FIG. 7c

ENDOTRACHEAL TUBE CONSTRUCTION AND METHOD FOR INTUBATING A PATIENT

FIELD OF THE INVENTION

This invention relates to an improved endotracheal tube construction and to a method for intubating a patient which reduces the risk of forming a kink in or collapsing the tube during use. It relates more particularly to an endotracheal tube construction in which a cuff inflating lumen is disposed in that portion of the endotracheal tube which is subjected to tension as the tube is anatomically curved during intubation. The invention also relates to an improved endotracheal tube construction and method for biasing a suction catheter or the like toward or into a selected one of a patient's bronchial openings.

BACKGROUND OF THE INVENTION

As disclosed in my earlier U.S. Pat. No. 4,850,348, there are many types of endotracheal tubes known to the medical profession, and many types of known apparatus for keeping the tubes in place in a patients oral cavity and trachea. However, it has been found that a number of these tubes may have life threatening consequences. One of the more serious consequences is the deficiencies of the materials selected for use in manufacturing the tubing. Some of the plastic materials used for making endotracheal tubing are not heat stable in their physical characteristics at body temperatures and do not remain firm enough at those temperatures to retain their desired shapes while being inserted, and while in place. Sometimes a tubing will collapse and/or kink, causing irritation if left in place, and more importantly, significantly reducing the rate of flow of air, oxygen mixture, etc., that can flow through the tube. The total volume of fluid flow per unit of time through a tube is given by Poiseuille's law as follows:

$$\frac{dV}{} = \frac{\pi}{8} \quad \frac{R^4}{n} \quad \frac{(p_1 - p_2)}{L} \text{, where}$$

V=volume of flow.
R=radius of the tube.
$p_1$ and $p_2$ are the pressures at the respective ends of the tube.
n=viscosity of the flowing fluid.
L=the length of the tube.

From this equation it is seen that any slight restriction in the radius R of the tube can have a significant reduction in the rate of flow through the tube since the radius is raised to the fourth power.

Additionally, it is seen that the rate of flow is inversely proportional to the length of the tube. Therefore, for a weak patient who does not have the strength to overcome any significant resistant to breathing, not only must the tube remain uniform in cross section throughout its length, but the tube must be as short as possible.

These basic physical considerations were addressed in my aforementioned patent. For example, an endotracheal tube according to my earlier invention has unique physical characteristics so that it will not kink or collapse during intubation or while in place. The material from which the tube is made is stable in its physical characteristics at body temperatures and will not usually collapse or kink under conditions to be experienced in use. Contributing to the maintenance of the cross sectional shape of the tube is a judicious selection of wall thickness relative to the tube diameter with a diameter to wall thickness ratio in the range of 3 to 4:1 to permit the tube to readily bend through at least 90° without the wall collapsing. To assure that the tube is of minimum possible length, the deflated cuff or balloon at the distal end of the tube is positioned in the trachea just below the vocal cords. The balloon then is inflated and the tube passed through and secured in an oral bite piece. The excess length of tubing that extends beyond the bite piece then is severed. This procedure assures that the tube is as short as it can be made without irritating or damaging the vocal cords, thereby providing the minimum value of L for the above equation.

Notwithstanding the above, endotracheal tubes which are presently on the market still have a tendency to kink or collapse when subjected to body temperature. Accordingly, it is highly desirable to further reduce any such tendency. Nevertheless, it has been found that in conventional endotracheal tubes having a permanent curve therein the cuff inflation lumen follows a pathway which is on the inside of the curve, the area which is under compression. In addition, it has been found that in those tubes which do not include a permanent curve, the tubes are designed so that during intubation, the cuff inflation lumen is positioned on the inside of the anatomical curve. It has also been found that the initiation of a kink or tube collapse frequently occurs in that portion of the tube which is under compression as the tube is bent to comply with the anatomical curve of the patients oral cavity and trachea.

There is one other problem associated with the prior art endotracheal tubes. The problem relates to their use with a suction catheter for removing residual secretions from one or the other or both of a patient's bronchial openings. The problem is that prior art tubes bias an end of the suction catheter toward one of a patient's bronchial openings, and it is difficult to position the catheter to remove residual secretions from the other opening. Some prior art tubes include a Murphy's eye, i.e. an opening in the back side of a beveled tip so that the catheter end can pass through the Murphy's eye and into the other opening. However, the Murphy's eye may act as a curette and damage a patient's trachea. In addition, it is still quite difficult for an attendant to position the end of the suction catheter to remove secretions from the desired area.

It is presently believed that an improved endotracheal tube construction and method in accordance with the present invention will significantly reduce the likelihood of tube kinking or collapse during intubation of a patient. It is also believed that the tubes in accordance with the present invention can be economically manufactured and sold at a competitive price and at the same time provide all of the advantages provided by the tubes in accordance with my aforementioned invention, i.e. U.S. Pat. No. 4,850,348, which is incorporated herein in its entirety by reference.

The improved endotracheal tubes in accordance with the present invention also facilitate the use of a suedon catheter for removing residual secretions from one or the other or both of a patient's bronchial tubes. To be more specific, the improved endotracheal tube construction disclosed herein enables a physician or nurse to readily position the end of a suction catheter in or toward a selected bronchial opening and after removing any residual secretion to reposition the tip to evacuate the other openings.

SUMMARY OF THE INVENTION

In essence, the present invention contemplates a kink resistant endotracheal tube comprising a relatively flexible elongated tubular member having distal and proximal ends with a distal end that terminates in a chamfered or beveled opening. The tubular member includes a wall of a preselected thickness which defines a first or major passageway between the ends of the tubular member. The tubular member also includes a cuff inflating lumen, i.e. a second or minor passageway which extends along and through the wall parallel to the first or major passageway. The endotracheal tube also includes an inflatable cuff or balloon of a gas impervious material secured to the exterior surface of the tubular member at the distal end thereof. In a preferred embodiment of the invention this balloon or cuff is immediately adjacent to the opening in the distal end and has a design as shown in my aforementioned patent. The balloon is connected to or communicates with the cuff inflating lumen for inflation by a flow of gas or air through the lumen. Means are also provided for positioning the tubular member within a patient's trachea so that a portion thereof is curved in order to comply with the anatomical curve of the patient's oral cavity and trachea to define inner and outer pathways. Along the inner pathway, the tube is under compression and along the outer pathway the robe is under tension. In addition, the means for positioning the tubular member also positions it so that the cuff inflation lumen follows the outer pathway, i.e. is within the wall pension of the tubular member which is under tension.

In one preferred embodiment of the invention, the tubular member also includes a thicker wall portion adjacent to the cuff inflating lumen which extends along the length of the cuff inflating lumen to further reduce the likelihood of the tube forming a kink or collapsing as it reaches body temperature.

The invention also contemplates a novel method of intubating a patient which includes the step of providing an endotracheal robe as described above. The tube also includes a chamfered or beveled end or opening with a closed or back section of the opening extending beyond its opposite side to thereby form a face of the opening. This beveled opening is immediately adjacent to the cuff and aligned with the cuff inflating lumen so that an extension of the lumen would intersect with the tip of the beveled end. In intubating a patient, the endotracheal tube is positioned so that the beveled end is positioned to pass easily through the vocal cords with out damaging the vocal cords. Then the tube is rotated so that the elongated or back portion of the opening is positioned adjacent to the patient's back. In this way, the cuff inflation lumen will be positioned in that portion of the robe which is under tension.

In a second preferred embodiment of the invention, the endotracheal robe includes means for positioning the tubular member so that a portion thereof is curved to fit a patient's anatomical arch and with the open face of the beveled tip facing one of the patient's bronchial openings. This means which includes the wall thickness and stiffness rotates the open face of the beveled tip to face the patient's other bronchial opening by twisting the proximal end, i.e. the portion of the robe which extends out of a patient's mouth or nose. The robe is constructed and arranged so that the beveled tip can be rotated while maintaining the curve following the anatomical arch without keeping or otherwise obstructing the passageway. Having the open face of the beveled tip facing a selected bronchial opening biases the end of the suction catheter toward or into that opening. Then, if a physician or nurse wants to remove residual secretions from the other bronchial opening, the end of the suction catheter can be retracted and the tip of the tube rotated to bias the catheter toward the other opening.

The invention will now be described in accordance with the accompanying drawings wherein like reference numerals have been used to designate like parts.

BRIEF DESCRIPTION OF THE DRAWINGS

FIG. 6A is an enlarged cross sectional view of an endotracheal tube according to a preferred embodiment of the invention taken along lines 6—6 in FIG. 5;

FIG. 6B is an enlarged cross sectional view of a prior art endotracheal tube for comparison to the endotracheal tube shown in FIG. 6A; and FIGS. 7A, B and C are schematic illustrations showing the position of an endotracheal tube according to the present invention as it passes through a patient's vocal cords and in the trachea.

DETAILED DESCRIPTION OF THE PREFERRED EMBODIMENT OF THE INVENTION

Figure 1:
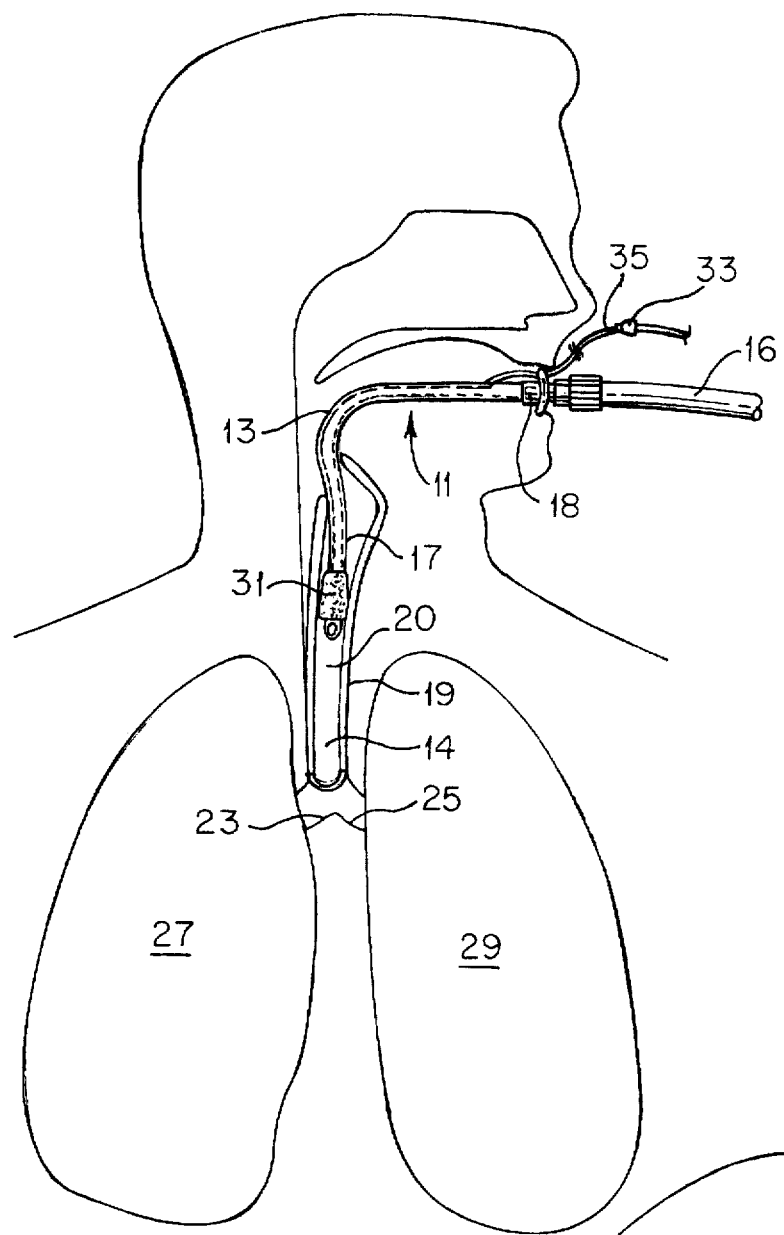
FIG. 1 is a schematic illustration of an endotracheal tube in accordance with the present invention positioned in a patient.
Figure 2:
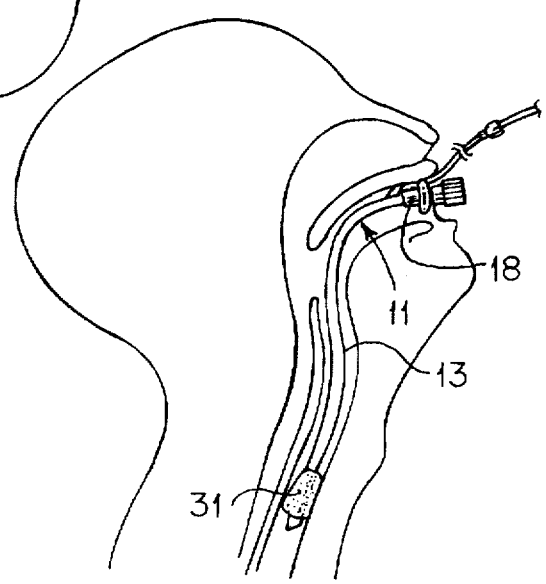
FIG. 2 is a schematic side view of an endotracheal tube according to the invention as used in a typical intubation of a patient.

As shown in FIGS. 1 and 2, an endotracheal tube 11 includes a length of tubing or tubular member 13 having a distal end portion 17 which is constructed and arranged for oral intubation in a patient's trachea as will be described hereinafter. The tubular member 13 also includes a proximal end portion 16 which passes through a patient's mouth and into and through a bite block 18.

The tubular member 13 is sufficiently flexible to bend and conform to a patient's anatomy but may include a permanent bend which generally conforms to the anatomical curve between the oral cavities and the trachea. Those tubes which include a permanently curved section are still somewhat flexible in that portion in order to conform to the anatomical curve of a specific patient. However, in either case, the tubing has the physical properties which are selected to reduce the likelihood of kinking or collapsing during insertion and while in place as will be described below.

As shown in FIG. 1 and as disclosed in my aforementioned patent, the tubing should be able to bend through substantially 90° without the wall collapsing or kinking. The problem is that the tube is more likely to kink or collapse at body temperature. For this reason, the presently preferred tubing is made from a medical grade silicon material so that the physical characteristics of the tube are relatively stable at human body temperature. Such characteristics include a hardness in the range of about 80 durometer. In one size of tubing, made for oral intubation, the inner diameter is 0.32" (8 mm) and the wall thickness is about 0.040" (1 mm). These dimensions are representative.

A presently preferred composition of silicone had the following constituent materials, and approximate proportions by weight.

Dimethyl silicone: 90%

Inert silica filler: 10%

Platinum salts as catalyst or curing agent: less than 1%

Conventional mixing, extrusion and curing methods may be used and are well known to those skilled in the art.

Although the above described silicone material is presently preferred, other materials having the described characteristics, i.e. a durometer of about 80 may be used. For example, a medical grade, biocompatible polyurethane, polyethane or other material may be used if a sufficient durometer rating can be obtained. In essence, it is important the physical characteristics of the material are selected to provide sufficient stiffness and resistance to kinking with the minimum wall thickness. Thus, in selecting the wall thickness and physical characteristics of a material, care should be exercised in constructing a tube which will not kink at normal human body temperatures and which allows the tip of the tubular member to be rotated by twisting the portion of the tube which extends out of the mouth or nose of a patient. For example, in prior art tubes, there is insufficient stiffness at human body temperatures to transmit the torque from one end of the robe to the other. In other words, it would be like twisting a piece of hot spaghetti. In other robes, the tubes are too rigid, and it is not possible to rotate the tip by twisting the end because the anatomical arch prevents the rotation of the tube.

Figure 3:
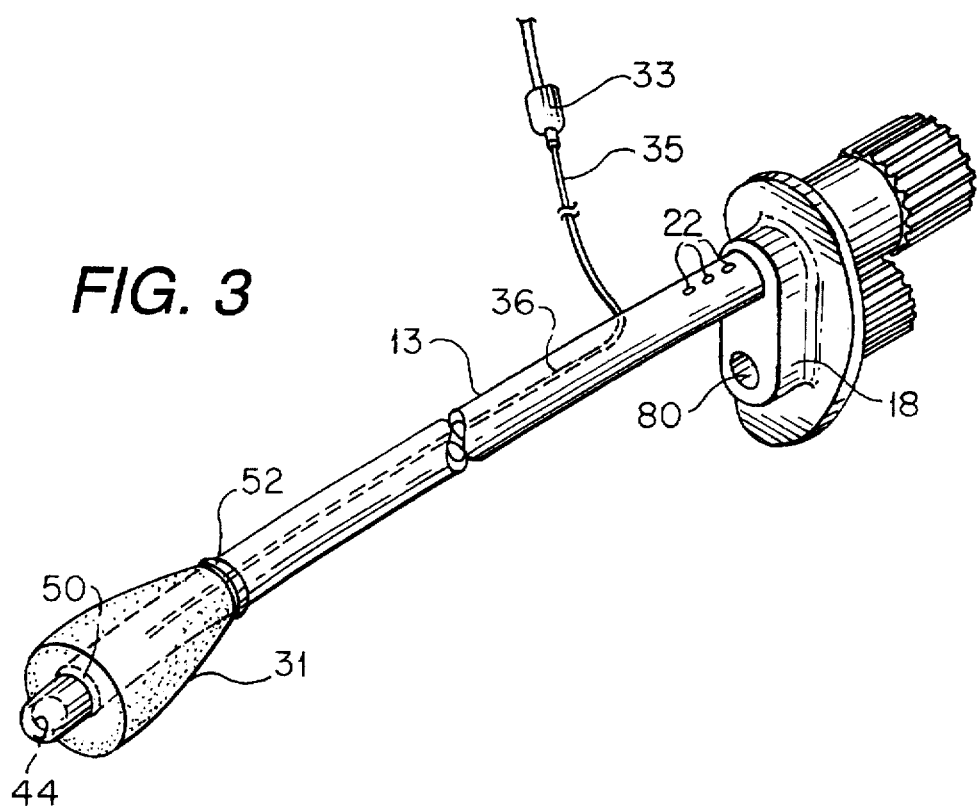
FIG. 3 is a more detailed illustration of the endotracheal tube shown in FIGS. 1 and 2.

Tubular member 13 is of one-piece, extruded construction and has smooth exterior and interior surfaces throughout. As best seen in FIGS. 2 and 3, the distal end of the tube or tubular member 13 usually is cut diagonally, i.e. at an acute angle to the central axis of the tube. As illustrated in FIG. 1, the tube is flexible and conforms to the patient's anatomy when inserted. It is a characteristic of the tube of this invention that it will not kink or collapse while being intubated or after being in place for great lengths of time.

The distal portion 17 of the endotracheal robe is provided with an expandable cuff or balloon 31 of a gas impervious material such as a thin sheet of silicone material of the type described above. Cuff 31 is inflated by means of a pilot balloon 33 connected to the cuff by an external robe 35 and internal passage 36 in the wall of the tubular member 13, as is known in the art. See FIG. 2. When the cuff 31 is inflated to engage the wall of trachea 19, air or other gases pass to and from a patient's lungs, 27, 29, through the bronchi 23, 25, and through the interior of the tubular member 13. The proximal end 16 of the tubular member 13 is adapted to be connected to a ventilator or oxygen source and/or a suction device in a conventional manner.

Figure 5:
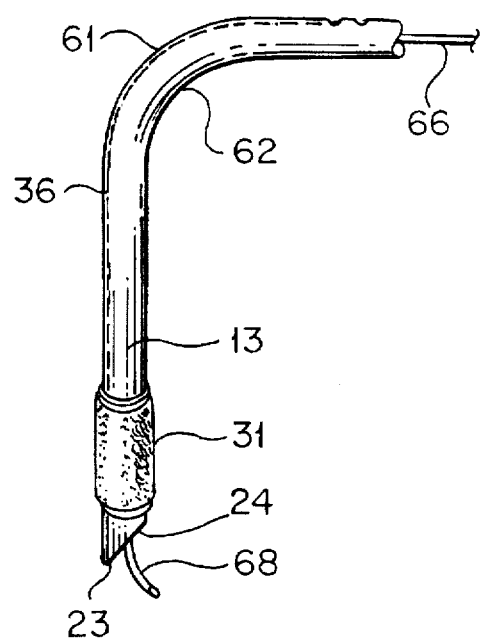
FIG. 5 is a side elevational view of a curved segment of an endotracheal tube according to the invention which illustrates the position of a cuff inflating lumen and a suction catheter contained therein.

Notwithstanding the use of the above materials and dimensions, the endotracheal tubes have been known to kink or collapse during use. For this reason, it is believed to be vitally important to incorporate an improved construction which will further reduce the likelihood of a kink or tube collapse during use. To this end, the construction of the endotracheal tube 11 has been redesigned. For example, it has been found with conventional tubes, that a kink or collapse is initiated with a small or minor lumen in the tube wall when that wall is subjected to compression. In conventional tubes, the walls in this area are customarily subjected to compression when the tube is bent since the lumen is positioned in that portion of the tube wall which is on the inside of the curve as the tube follows the anatomical curve of a patient. In other words, in conventional tubes, the minor lumen is located in that portion of the tube which is subjected to the maximum amount of compression. In addition, placing the lumen in the wall of the tubular member reduces the effective strength of the wall in that portion. Then as this portion of the wall is subjected to compression during bending of the tube, the tube kinks or collapses. As shown more clearly in FIGS. 5 and 6A, an endotracheal tube 11 in accordance with the present invention includes a major passageway 20 between its distal and proximal ends 14 and 16. As shown in FIG. 5, the tubular member 13 includes an inflatable cuff 31 and a minor lumen or internal passage 36. Means such as a plurality of dots 22 (FIG. 3) on the outer surface of the tubular member 13 may be used in positioning the internal passage 36 during intubation as will be described later.

The distal end of the cuff 31 has an annular end 40 that is secured in contact with the tubular member 13 and faces in the direction of the proximal end of tubular member 13. The material of the cuff extends toward the distal end of the tube to overlap the annular end 40 as described in more detail in my aforementioned patent. For example, the distal end of the cuff should be as close as possible to the open end 44 of the tubular member 13 without interfering with the opening.

Figure 4:
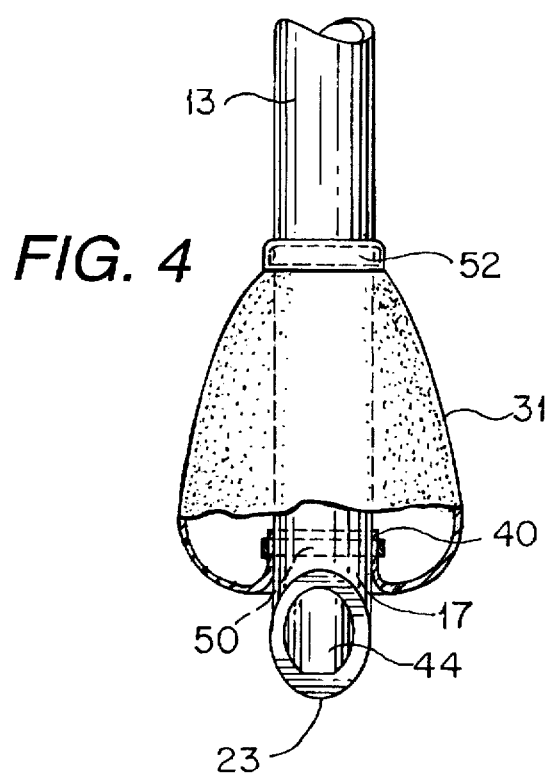
FIG. 4 is a simplified illustration of a distal end of the endotracheal tube in accordance with the present invention.

As shown in FIG. 4, bands of radio opaque material 50 and 52 (see FIG. 4) are at or adjacent the respective ends of the cuff 31 to define the opposite end region thereof. In addition, the proximal end of tubular member 13 passes through and is secured to an oral bite piece 18 that is shown in FIG. 3. For example, a shaped end is received in the patient's mouth. This bite piece 18 may also include a second passageway 80 and is made of any suitable material as disclosed in my aforementioned patent.

A key feature in the present invention resides in the positioning of the minor lumen or internal passage 36 in that portion of the tubular member 13 which is subjected to tension when the tube is curved in order to conform to the patient's anatomy, the anatomical curve between the oral cavity and the trachea. To be more specific, the tubular member 13 may be permanently curved as shown in FIG. 5. The curve is formed in a conventional manner as will be well understood by those skilled in the art. The curve then defines an outer pathway 61, i.e. on the outside of the curve and an inner pathway 62 on the inside of the curve as shown in FIG. 5. In forming a curve in the tubular member 13, that portion of the tubular member 13 which is adjacent to the inner pathway 62 is compressed while the portion along the outer pathway 61 is stretched or under tension. Also, assuming that the curve approximates the radius of a circle, the inner pathway will have a smaller radius than the outer pathway and would, therefore, be more likely to initiate a kink in the tube. Therefore, the positioning of the minor lumen in the present invention, i.e. placed on the larger radius produces a stronger wall reducing the likelihood of kinking.

Also as illustrated in FIG. 5, the internal passage 36 shown by dotted lines is aligned with the elongated portion 23 of the beveled tip 24. In other words, if the lumen were extended beyond the coil 31, it would intersect with the extended portion of the tip 24. As shown in FIG. 5, a suction catheter 66 for use in combination with the endotracheal tube extends through the tubular member 13 with a distal end of the catheter 68 extending outwardly from the beveled tip 24. As shown, the distal end 68 is biased in a first direction, i.e. inward a selected bronchial opening by the beveled tip 24. Therefore, when it is desired to remove residual secretions from the patient's other bronchi, the tip is rotated in order to bias the distal end 68 toward that opening.

In addition to the above, it is also desirable to provide a thickened wall section adjacent to the minor lumen or passageway 36 as shown more clearly in FIG. 6A. As shown therein, the thicker wall section is defined by a D-shaped inner cross section and a circular outer cross section with the passageway 36 passing through the tubular wall section between the flat portion 26 of the D (the inner wall) and the outer surface 28. In the preferred embodiment, the thickness of the wall between the passage 36 and the flat portion 26 is greater than that which is between the passage 36 and the outer surface 28. For comparison, FIG. 6B shows a conventional endotracheal tube. As shown therein, a minor lumen is in the lower portion of the tube and because of its size, reduces the amount of material which is subject to compression thereby weakening the tube and making it more susceptible to kinking or collapse.

FIG. 7 illustrates the positioning of the inner lumen or passage 36 and tip 24 of the tubular member 13 as a patient is intubated. As shown in FIG. 7A, the beveled edge of the tip is angled with respect to the vocal cords in order to be more easily slipped therebetween. Thereafter, the tube is forced downwardly through the trachea and rotated, as illustrated by the arrow on FIG. 7B, to bring the minor lumen or passageway 36 on the outer pathway 61 as shown in FIG. 5. When so positioned, an open face of the beveled tip 24 will face the front or chest of a patient while the elongated or back portion is toward a patient's back. With respect to FIG. 7A, the apex 70 of the vocal cords 72 point toward the front or chest of a patient while the base 74 is toward a patient's back.

In one embodiment of the invention, means for maintaining a permanently curved portion of the tubular member 13 are provided. This curved portion is still somewhat flexible so that it accommodates a specific patient, i.e. the anatomical curve of that patient. The means may, for example, include the selection of wall thickness, the stiffness of the tubular member 13, molding and forming techniques and temperatures, subsequent heat treatment or the like as will be well understood by those skilled in the art. In addition, the curved portion should be sufficiently rigid at human body temperature, so that the tip 24 may be rotated from one bronchial opening to the other by twisting the proximal end 16 of the tubular member 13, i.e. by twisting that portion of the tubular member 13 which extends out of a patient's mouth or nose.

In a preferred embodiment of the invention, the endotracheal tube has structural integrity along its length except for the inflation lumen. For this reason, such tubes are less likely to kink or collapse than those prior art tubes which include a longitudinal opening for a radio opaque marker running along the length of the tube.

While the invention has been described in connection with accompanying embodiments, it should be recognized that changes and modifications may be made therein without departing from the scope of the appended claims.

What is claimed is:

1. A kink resistant endotracheal tube comprising a flexible elongated tubular member having distal and proximal open ends, a curved portion and a wall thickness of about 0.040 inches defining a central major passageway and a secondary minor lumen extending along and through said parallel to said passageway;

said tubular member including a thickened wall portion, adjacent said secondary minor lumen, forming a generally D-shaped internal cross-section and a circular external cross-section in said tubular member with said secondary minor lumen extending through the wall of said tubular member at a position between the flat side of the D and the external circular portion, so that the wall thickness of the tubular member is thicker in the area of the secondary minor lumen, and a second portion of said tubular member opposite from said thickened wall portion having structural integrity;

means including said curved portion in said tubular member for positioning said tubular member within a patient's trachea, so that a portion thereof defines an inner pathway wherein said tubular member is under compression and an outer pathway wherein said tubular member is under tension, and wherein said thickened wall portion and said secondary minor lumen is within that portion of said wall which is under tension, so that the tubular member will not kink or collapse during intubation of a patient;

an inflatable cuff or balloon of a gas impervious material secured to the exterior surface of said tubular member at the distal end thereof and communicating with said secondary minor lumen for inflation by a flow of a gaseous medium through said lumen; and means for inflating said cuff or balloon for positioning the endotracheal tube within a patient's trachea.

2. A kink resistant endotracheal tube according to claim 1 in which said tubular member is formed of non-toxic material that is heat stable in its physical characteristics within the range of human body temperature to be encountered in use, has a hardness of about 80 durometer, and an inside diameter-to-wall thickness ratio of about 8:1 so that the member is non-collapsible during insertion and while in place in the trachea and is capable of withstanding a 90° bend without collapsing.

3. A kink resistant endotracheal tube according to claim 2 wherein the thicker wall section is positioned along the wall thickness between the minor lumen and the internal surface of the tubular member is greater than the wall thickness between the lumen and the exterior surface.

4. A kink resistant endotracheal tube for use with a suction catheter comprising a flexible elongated tubular member having distal and proximal open ends and a curved portion therebetween, said curved portion defining an inner pathway wherein said tubular member is under compression and an outer pathway wherein said tubular member is under tension, a wall of a thickness of about 0.040 inches defining passageway between said distal and proximal open ends and a beveled tip defining an open face at said distal end;

said tubular member including a cuff inflation lumen extending along and through said wall parallel to said passageway and within that portion of said wall which is under tension;

an inflatable cuff or balloon of a gas impervious material secured to the exterior surface of said tubular member at the distal end thereof communicating with said cuff inflation lumen for inflation by a flow of gaseous medium through said lumen; and means including the curved portion, the wall thickness and stiffness of said tubular member for positioning said tubular member within a patient's trachea so that a portion thereof is curved with said open face of said beveled tip facing one of the patient's bronchial openings and for rotating said open face of said beveled tip to face the other of said patient's bronchial openings without forming a kink or obstruction in said passageway by twisting the proximal end of said tubular member so that one end of a suction catheter may be biased into a selected one of the patient's bronchial openings for removal of residual secretions therefrom.

5. A kink resistant endotracheal tube for use with a suction catheter according to claim 4 wherein said inflatable cuff is adjacent to said beveled tip.

6. A kink resistant endotracheal tube for use with a suction catheter according to claim 4 wherein said tubular member defines a solid wall which is free of any opening between said inflatable cuff and said beveled tip.

7. A kink resistant endotracheal tube for use with a suction catheter according to claim 4 wherein said beveled tip defines a solid wail which is free of any openings other than its open face.

8. A kink resistant endotracheal robe for use with a suction catheter according to claim 7 wherein said curved portion defines an inner pathway wherein said tubular member is under compression and an outer pathway wherein said tubular member is under tension and said cuff inflation lumen is within that portion of said wall which is under tension when said beveled tip is in a first position.

9. A kink resistant endotracheal tube for use with a suction catheter according to claim 4 which includes a thickened wall portion adjacent to said cuff inflation lumen.

10. A kink resistant endotracheal tube for use with a suction catheter according to claim 9 in which said tubular member is formed of non-toxic material that is heat stable in its physical characteristics within the range of human body temperature to be encountered in use, has a hardness of about 80 durometer and an inside diameter-to-wall thickness ratio of about 8:1 so that the member is non-collapsible during insertion while in place and during rotation of said beveled tip by twisting said proximal end.

11. A method for intubating a patient for removing secretions from the bronchial tubes of the patient comprising the steps of:

(a) intubating a patient with an endotracheal tube having distal and proximal ends with an air passageway therebetween to thereby provide a curved section with a portion thereof under tension and a cuff inflation lumen parallel with the passageway and disposed in a wall of the tubular member which is under tension, an inflation cuff secured to an outer surface of the tubular member and communicating with the cuff inflation lumen for inflation by a flow of gas and including a beveled tip adjacent to the inflatable cuff so that the endotracheal tube passes through the vocal cords without damaging the cords and into the trachea of the patient so that the endotracheal tube follows the anatomical curve between the patient's oral or nasal passage and trachea;

(b) rotating said open faced beveled tip to face one of the patient's bronchial openings without forming a kink or obstruction in the passageway by twisting a portion of the tube that extends out of the mouth or nose of the patient;

(c) inserting a suction catheter through the air passageway and biasing the suction catheter into the patient's bronchial opening; and (d) removing any secretions from in or around the patient's bronchial opening.

12. A method for intubating a patient and for removing sections from the patient's bronchial tubes or the like according to claim 11 which includes the additional step of:

rotating the open faced beveled tip to face the patient's other bronchial opening by twisting a portion of the tube that extends out of the mouth or nose of the patient to thereby bias the suction catheter into the other of the bronchial openings and removing any secretions from in or around the patient's other bronchial tube.

13. The combination of a kink resistant endotracheal tube and a suction catheter for removing secretions from in or around a patient's bronchial tubes, the combination comprising:

a flexible elongated tubular member having distal and proximal open ends and a curved portion between said ends, said cutting portion defining an inner pathway wherein said tubular member is under compression and an outer pathway wherein said tubular member is under tension, a wall of a thickness of about 0.040 inches defining a passageway between said distal and proximal open ends and a beveled tip defining an open face at said distal end;

a suction catheter extending through said central passageway with one end thereof extending out of said distal end and biased in a first direction by said beveled tip and with its opposite end extending out of said proximal end of said tubular member and adapted for connection to a vacuum source;

said tubular member including a cuff inflation lumen extending along and through said wall parallel to said passageway and within that portion of said wall which is under tension;

an inflatable cuff of a gas impervious material secured to the exterior surface of said tubular member at the distal end thereof communicating with said cuff inflation lumen for inflation by a flow of gaseous medium through said lumen; and means including the curved portion, the wall thickness and stiffness of said tubular member for positioning said tubular member within a patient's tracheal so that a portion thereof is curved with said open face of said beveled tip facing one of the patient's bronchial openings to thereby bias the end of said suction catheter which extends through said distal end of said tubular member toward the one of the patient's bronchial openings, and for rotating said open face of said beveled tip to face the other of said patient's bronchial openings to thereby bias the end of said suction catheter which extends through said distal end of said tubular opening toward the other of said bronchial openings without forming a kink or obstruction in said passageway by twisting the proximal end of said tubular member so that either of the patient's bronchial tubes can be selectively subjected to suction for removal of residual secretions therefrom.

14. The combination of claim 13 wherein said tubular member includes a thickened wall portion adjacent to said cuff inflation lumen.

* * * * *